United States Patent [19]

Brossard

[11] Patent Number: 5,222,979
[45] Date of Patent: Jun. 29, 1993

[54] METHOD OF CHIROPRACTIC TREATMENT AND SHAPED BLOCKS THEREFOR

[76] Inventor: André Brossard, 2070 St-Hubert, Montréal, Quebec, Canada, H2L 3Z5

[21] Appl. No.: 785,934

[22] Filed: Oct. 31, 1991

[51] Int. Cl.⁵ ............................................. A61F 5/00
[52] U.S. Cl. ...................................... 606/240; 5/648; 5/925
[58] Field of Search .................... 128/845; 602/32; 606/237, 238, 240; 5/466, 630, 632–633, 646–648, 922, 925

[56] References Cited

U.S. PATENT DOCUMENTS

| | | | |
|---|---|---|---|
| 3,111,944 | 11/1963 | Puckett | 606/240 |
| 3,995,846 | 12/1976 | Frick | 5/648 X |
| 4,397,052 | 8/1983 | Lund, III | 5/632 X |
| 4,475,542 | 10/1984 | Brossard | |
| 4,646,374 | 3/1987 | Shafer | 5/925 X |

Primary Examiner—Richard J. Apley
Assistant Examiner—Linda C. Dvorak
Attorney, Agent, or Firm—ROBIC

[57] ABSTRACT

A shaped block that can be used for chiropractic treatment. The block has a base, a rear end face, an upper face parallel to the base and merging with the upper edge of the rear end face, a rectangular front end face merging with the front end of the base, and an upper oblique portion between the upper face and the front end face inclined between 60° to 85°. The oblique portion has a first upper inwardly curved section descending from an inner edge of the upper face, an intermediate flat face portion following the first curved section and raised above the plane of the oblique portion, and lifted 7° to 9° at the lower end, and a lower curved section between the intermediate flat face and the second end face. Irregular faces connect these parts together into a block. The faces of the curved section are anti-skidding so as to engage human body portion under treatment while preventing it from sliding along the curved surfaces. The block is made of soft rubbery material. A handle may be provided at the rear end to manipulate the block. For treatment, the blocks are used in pairs. For a right handed person, one block is inserted underneath the person lying on his back so as to rest below the right ischium against the oblique portion of one block, the block being oriented transversely with the lower front end corner pointing towards the groin area of the body of the person, and the second block is inserted underneath the same person with the oblique portion immediately below the left ischium with the upper front end corner pointing towards the groin area.

1 Claim, 6 Drawing Sheets 5,222,979

METHOD OF CHIROPRACTIC TREATMENT AND SHAPED BLOCKS THEREFOR

BACKGROUND OF THE INVENTION a) Field of the Invention

This invention relates to a method of chiropractic treatment, and shaped blocks that can be used for such treatment. More particularly, the invention relates to a treatment whereby a muscular pelvic balance and spinal alignment stabilize in a non traumatic way, by, using blocks which promote relaxation in these muscular areas to reduce or eliminate the daily pains accumulated by musculo-vertical displacement or stress. Still more specifically, the invention relates to chiropractic blocks which are specially designed to be as comfortable as possible when in use, and are effective when used by the patient even after a short treatment period.

b) Brief Description of the Prior Art

In my U.S. Pat. No. 4,475,542 and its canadian counterpart no. 1,173,708, I discussed the problems resulting from the fact that a person always has a tendency to use the same side of the body when doing physical exercises or physical work. This produces a stress and affects the region of the lower lumbar vertebrae. The manifestations of this stress can take the form of lumbago, sciatic nerve pressure, leg cramps, leg pain, sleeping leg, stiff neck, torticolis, headaches, fever, constipation, general fatigue, and the like.

In the Patents mentioned above, there is disclosed a block of irregular shape in which the upper face is formed of and two inwardly curved sections, which are separated by a trapezoidal flat portion.

This block has proved to be very effective for the chiropractic treatment of discomforts as mentioned above. However, because it is normally made of relatively hard material, and above all because the curved sections are smooth and slippery, the treatment appears sometimes unpleasant and is not as successful as would be expected because a zone under treatment does not always remain in contact with the block. It would seem that because the skin and underlying muscles have a tendency to slide along the curved surfaces, cure is not always easy to achieve. In addition, the trapezoidal flat portion and curved sections as defined in the above Patent appear to lack in their function of relaxing the muscles.

OBJECTS AND SUMMARY OF THE INVENTION

It is therefore an object of the present invention to provide a block intended for chiropractic treatment which is comfortable and gives successful results even after a short period of use.

It is another object of the invention to provide a chiropractic block enabling a patient to take a chiropractic treatment while at home.

It is a further object of the invention to provide a chiropractic block which is easy to handle and utilize.

In accordance with the invention, a block is provided for chiropractic treatment, which comprises:

an elongated base having a front edge and a rear edge;

a rear end face projecting inwardly from the rear edge of the base and having an upper edge parallel to the base;

an upper quadrilateral face parallel to the base and merging with the upper edge of the rear end face, this upper face having an over edge opposite and parallel to the upper edge of the rear end face;

a front end face projecting upwardly from the front edge of the base;

an oblique portion extending between the upper face and the front end face, the oblique portion being generally inclined at about 60° to about 85° with respect to the vertical, and comprising:

a first upper inwardly curved section descending from the inner edge of the upper face;

a substantially intermediate flat quadrilateral face portion following the first upper curved portion;

the quadrilateral flat face portion being raised above the oblique portion and having a lower end so lifted as to form an angle of between about 7° to 9° with respect to a plane parallel to the oblique portion;

a second lower inwardly curved section between the intermediate flat face and the front end face; and irregular lateral faces connecting the base, the first and second curved sections, the flat portion, the upper face and merging into the front and rear end faces, wherein the block is made of soft rubbery material and the first and second curved sections are formed with anti-skidding means capable of engaging a portion of a human body while preventing this portion from sliding along the curved sections.

In accordance a preferred embodiment of the invention, the rear end face of the block comprises an upper vertical portion, a lower inclined portion merging with the rear edge of the base, and a triangular prism projecting from the inclined portion to define a holding means to handle the block. Preferably, the base, the upper face and the intermediate flat face portion are all trapezoidal, and all the edges of the block that can contact a portion of the body are rounded.

In accordance with another preferred embodiment of the invention, the anti-skidding means comprise rugosities formed on the surfaces of both curved sections.

In accordance with the invention, there is also provided a method of chiropractic treatment with a person lying on his back which comprises providing two blocks according to the invention, inserting one block underneath the person so as to rest below one ischium on one side of the person against the oblique portion of the block, the block being oriented transversely of the body of the person with the lower corner pointing towards the groin area, and inserting a second block underneath the person with the oblique portion of the block immediately below the ischium on the other side of the person, and the upper front corner pointing towards said groin area.

BRIEF DESCRIPTION OF THE DRAWINGS

The invention will now be illustrated by means of the annexed drawings, it being understood that they are given only for the purpose of illustration and not for restricting the scope of protection which is defined by the appended claims.

In the drawings.

DESCRIPTION OF A PREFERRED EMBODIMENT

Figure 1:
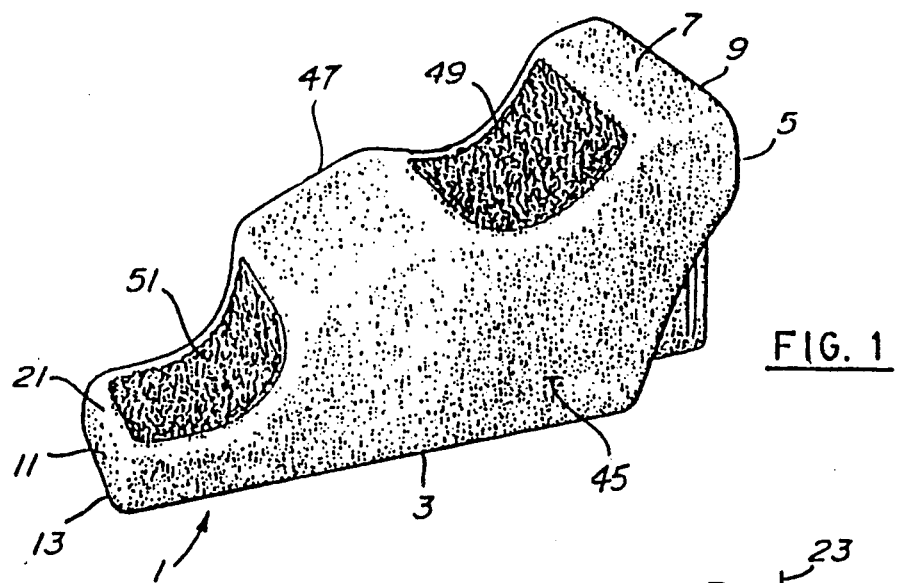
FIG. 1 is a perspective view of a chiropractic block according to the invention.
Figure 2:
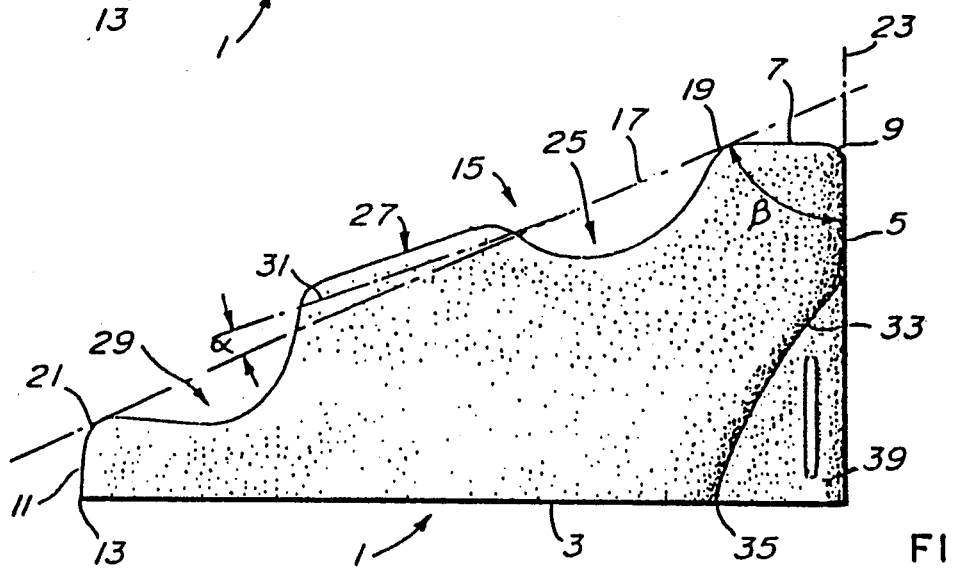
FIG. 2 is a view in elevation of the block illustrated in FIG. 1.
Figure 3:
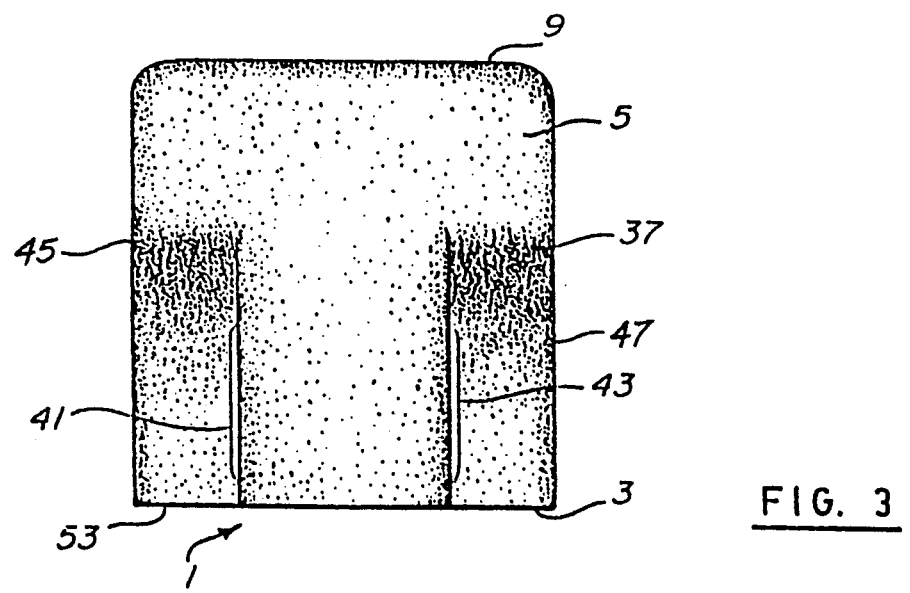
FIG. 3 is a rear end view of the same block.

The drawings, and more particularly FIGS. 1, 2 and 3, show that a chiropractic block 1 according to the invention, comprising a base 3 (suggested but not fully illustrated in FIGS. 1, 2 and 3) which has a trapezoidal shape. At the rear end of the block 1, a rear end face projects, which has an upper portion 5 that is substantially rectangular and is perpendicular to the base 3. An upper face 7 which has a trapezoidal shape and which is parallel to the base 3 and merges with the upper edge 9 of the rear end face 5, constitutes the top part of the block 1. At the front of the block, there is a substantially rectangular front end face 11 which is perpendicular to the base 3 and merges with the front edge 13 of the base 3.

A generally oblique portion 15 generally illustrated by broken line 17, and which extends from the front edge 19 of the upper face 7 and the upper edge 21 of the front face 11 defines the top or operating part of the block 1. It will be noted that the oblique portion 15 must form a specific angle $\beta$ with respect to the vertical 23 which in the present case is 65°. However this angle may vary between about 60° and about 85° as mentioned above.

Turning now to the oblique portion 15, it will be seen to consist of a first upper inwardly curved section 25 which descends from the inner edge (front edge) 19 of the upper face 7 and forms an arc of a circle until it merges with the intermediate trapezoidal flat face 27 which will be more specifically defined hereinbelow. The flat face 27 is followed by a second inwardly curved portion 29 which is slightly deeper than curved portion 25 and merges with edge 21 of the front face 11.

The flat face 27, as particularly illustrated in FIG. 1 is trapezoidal in shape, thus following the general outline of the base 3 and is slightly raised above the oblique portion to form an irregular but somewhat truncated pyramid portion 31 above line 17. In addition, the flat face 27 is slightly lifted at the lower end, as shown to form an angle $\alpha$ between about 7° and 9° with respect to a plane parallel to broken line 17 defining the oblique portion 15.

The rear end face of the block also comprises an inclined, slightly inwardly curved portion 33 which extends from the rear edge 35 of the base 3 to the lower edge 37 of the upper portion of this rear end 5. A triangular prism 39 projects from the inclined portion 33 and is provided with a pair of longitudinal catching devices 41,43, to enable handling of the block.

Finally, a pair of lateral irregular faces 45,47 connect the base 3 and all the other faces constituting the block 1.

A most important characteristic of the block 3 according to the invention is that both curved sections 25 and 29 are formed with surfaces that contain rugosities 49,51 thereby enabling to engage a body portion (not shown but in all practical cases a skin portion) while preventing it from sliding along each curved sections 29.

Another most important characteristic of the invention is that the block is made of a rubbery material whose selection is not critical but which must be chosen so as not to produced skin irritations and to be soft enough not to cause injuries while being sufficiently firm to prevent any substantial deformation when the chiropractic treatment is carried out. All this is well known to those skilled in the art. Advantageously, all the edges and corners of the block 1 are rounded as shown to provide more comfort.

Figure 4:
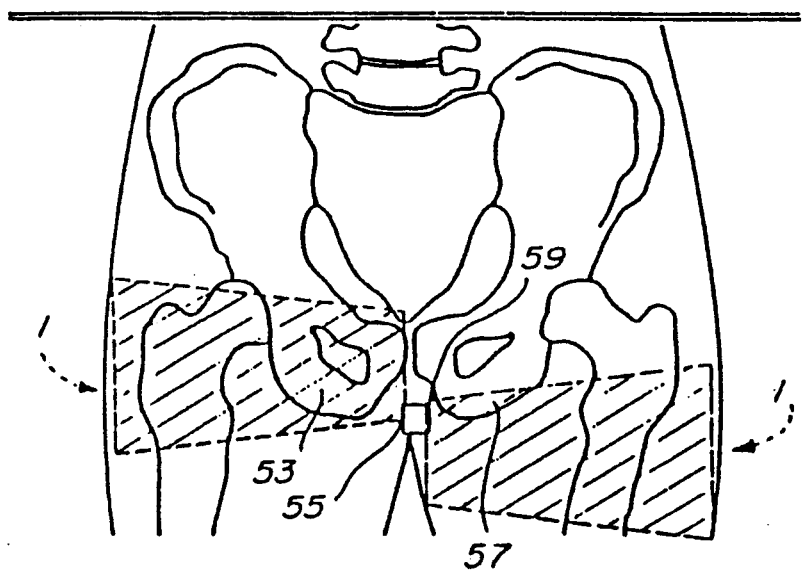
FIG. 4 is a view showing how a pair of blocks is used relative to the human body.

The method of treatment is slightly modified over that disclosed in my U.S. Pat. No. 4,475,542 and its Canadian counter patent No. 1,173,708. According to the present invention, one of the improved blocks described hereinabove is inserted underneath a right handed person under treatment as shown in FIG. 4 so as to rest below the right ischium 53 with the oblique portion 15 placed against the body. The block is oriented transversely of the body with the lower front end corner 55 pointing towards the groin are. The second block is inserted similarly below the left ischium 57 except that it is the upper front end corner 59 which points towards the groin area. With left handed people, the procedure is reversed.

Tests were made to compare the results of my previous block made of wood and the block according to the present invention and the results are as follows.

These tests were carried out on 28 year old man in good physical condition and health. The subject had no known record of neurological disorders nor of pathologies or accidents involving the lower limb musculature.

Electromyography (EMG) measurements were collected under three experimental conditions: before (i.e., PRE condition), during (i.e. BLOCK condition), and after (i.e., POST condition) the use of the blocks. The measurements were taken sequentially stating with the resting EMG. These measurements were conducted over two test periods. On the first test the rubber blocks according to the invention were tested first, whereas, on the second test the testing order was reversed, that is the wooden blocks where tested first.

The EMG activity was recorded through standard Beckman surface electrodes (Ag/AgCl). The electrodes were located over the belly of the following muscles on both legs: medial aspect of the soleus and semi-tendinosus. The active electrode was located over the estimated motor point, the reference electrode located 0.05 cm distally, while the ground electrode was located on a bony area (i.e., the head of the fibula). During the tests, measurements were taken only 10 seconds after the blocks were positioned (i.e., BLOCK-1 condition), and 60 seconds after (i.e., BLOCK-2 condition).

The exact same stages or conditions were repeated twice on each test: once for the rubber blocks (BR) and once for the wooded blocks (BB).

Figure 5A:
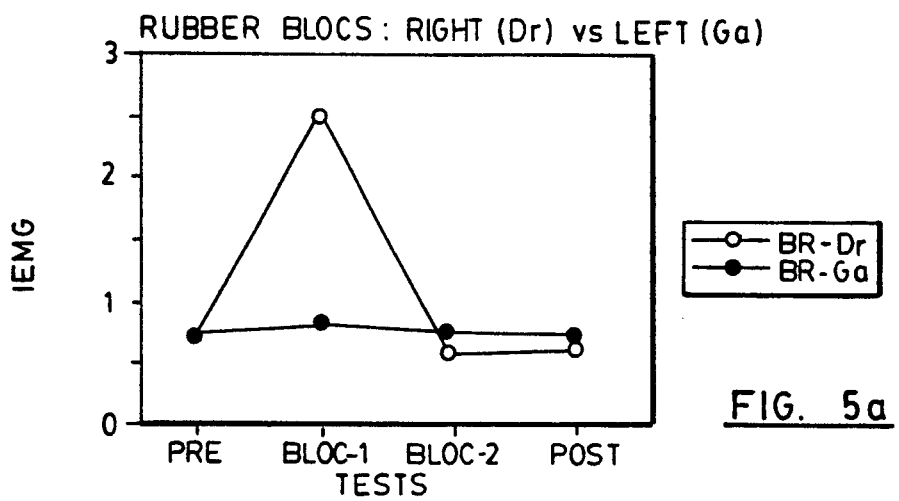
FIGS. 5a,b,c; 6a,b,c; 7a,b,c; and 8a,b are diagrams giving the IEMG response (integrated electromyographic response of a patient as a function of time with different blocks, including those according to the invention.
Figure 5B:
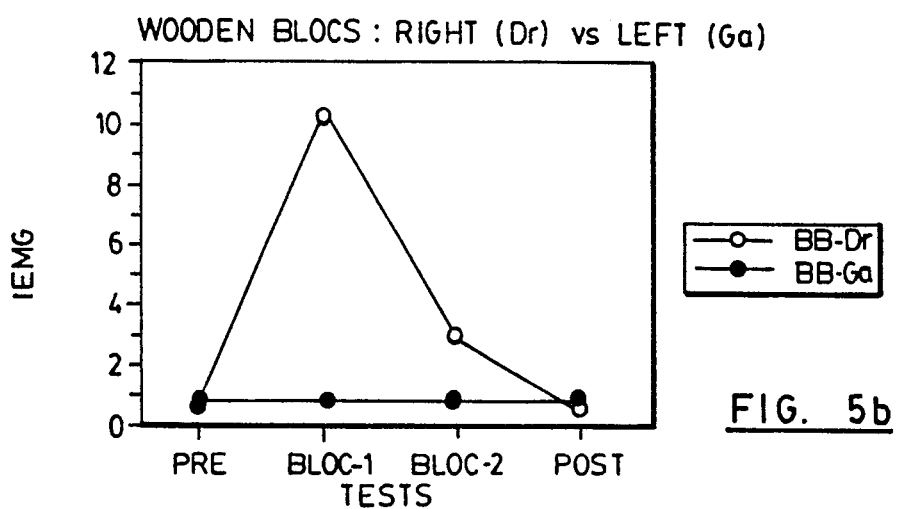
Figure 5C:
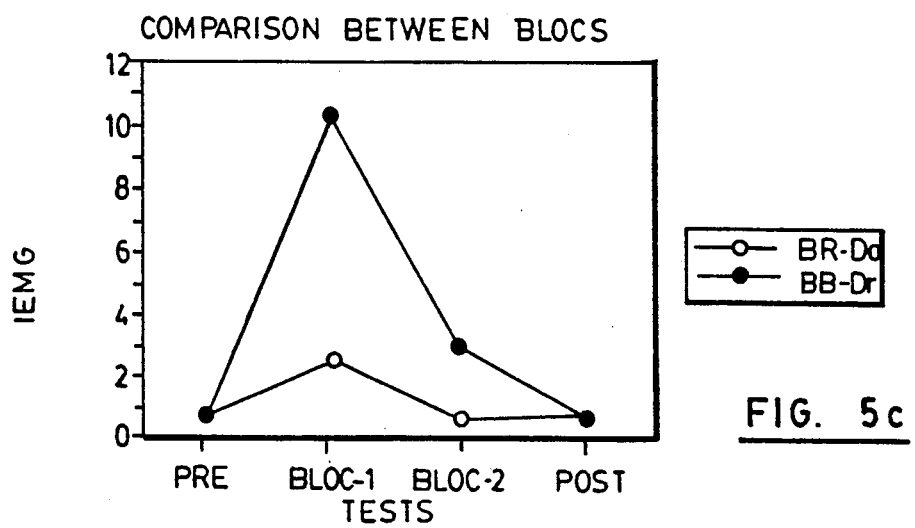
Figure 6A:
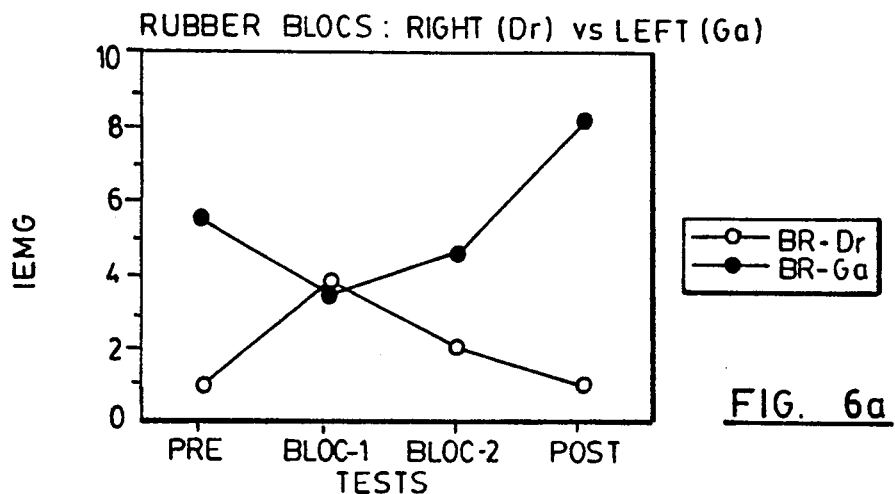
Figure 6B:
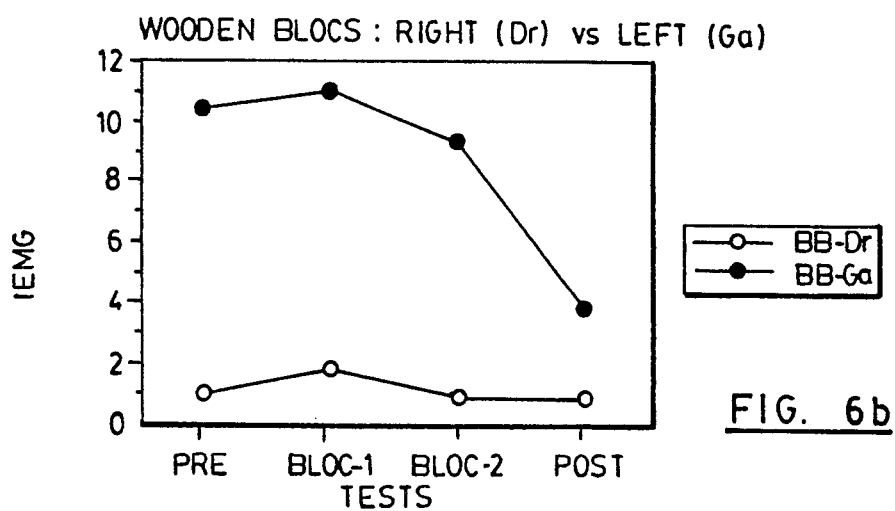
Figure 6C:
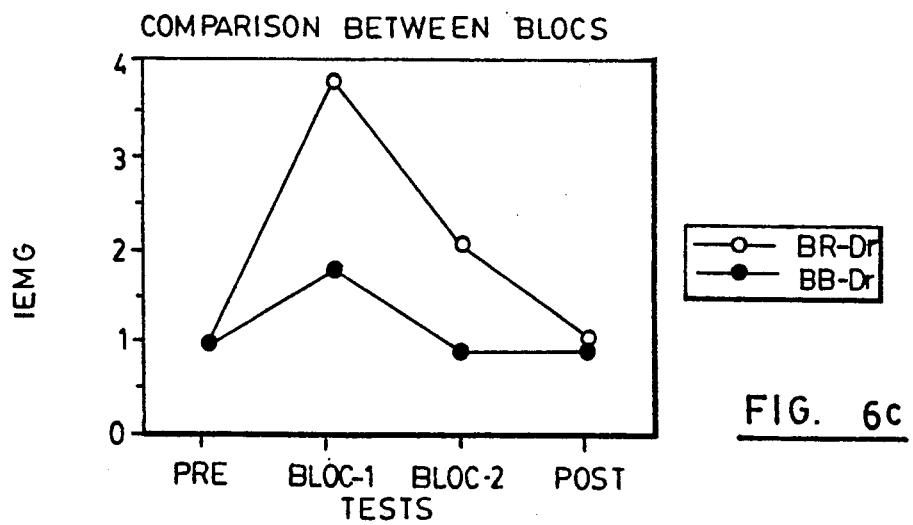
Figure 7A:
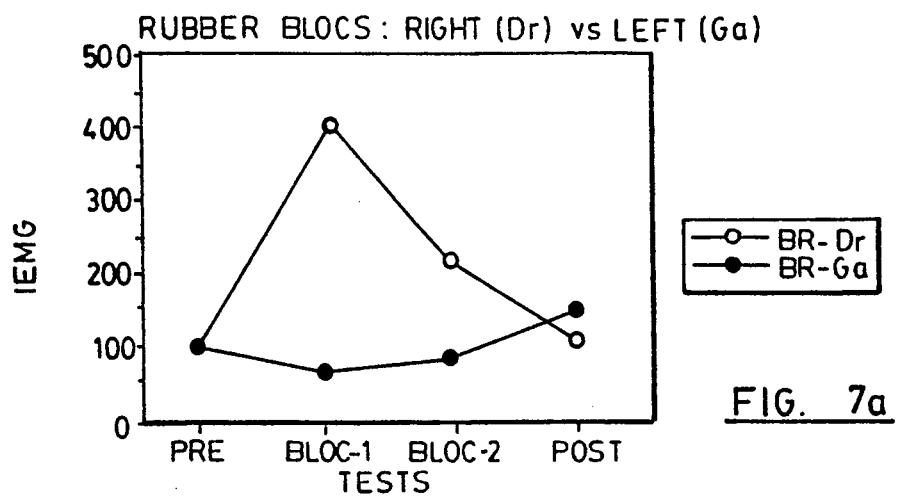
Figure 7B:
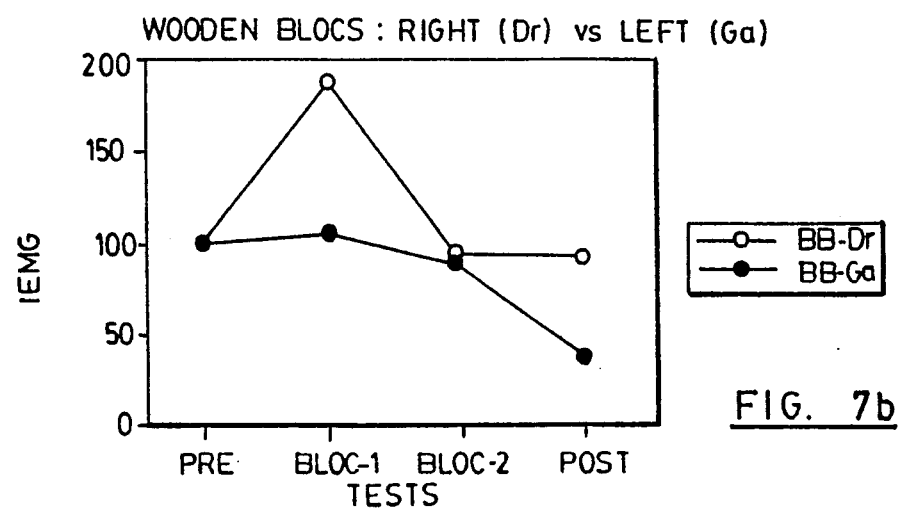
Figure 7C:
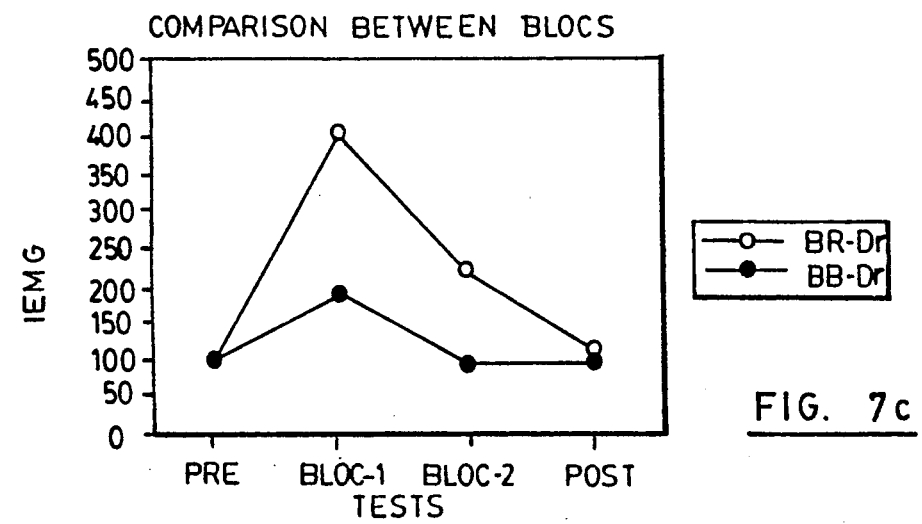

FIGS. 5 to 7 in which the results of the tests are reported are all organized in the same way. Each of them includes three graphs. The upper graph compares the two sides (i.e., Dr for right and Ga for left) for the rubber blocks, while the middle graph compares the two sides for the wooden blocks. The lower graph compares the two blocks on the right side, on which side differences were measured.

The results for the resting EMG are presented in FIGURES 5a to c and FIGS. 6a to c. The absolute levels of EMG for the first test are given in FIGS. 5 while the second test results are in FIGS. 6. FIGS. 7 show the second test results as a percentage of the PRE condition value. Finally, FIGS. 8a and b gives a comparison of the two tests.

A first characteristic that may be observed is the specificity of the block effects. No significant differences were obtained on the left side, whereas a significant difference ($p \leq 0.05$) was noted on the right side. Hence, on the right side, for the rubber blocks, there was no differences between the PRE and the POST conditions while there was a significant increase of 369% of the PRE value on the first test and of 40% on the second test. For the BLOCK-2 condition (i.e., 60 seconds later) no significant increase was found when that level was twice higher on the second test (i.e., BLOCK-2=202%).

For the wooden blocks, as for the rubber blocks, there are no differences between the PRE and POST conditions. However, there is an important increase in the resting EMG level when the blocks are in place. On the first test, the increase is of 1728% (i.e., 17 folds increase) at the BLOCK-1 condition, while the increase is of 495% for the same test in the BLOCK-2 condition. On the second test, the increase is much more modest, increase of 188% in the BLOCK-1 condition, and decrease of 94% in the BLOCK-2 condition.

Figure 8A:
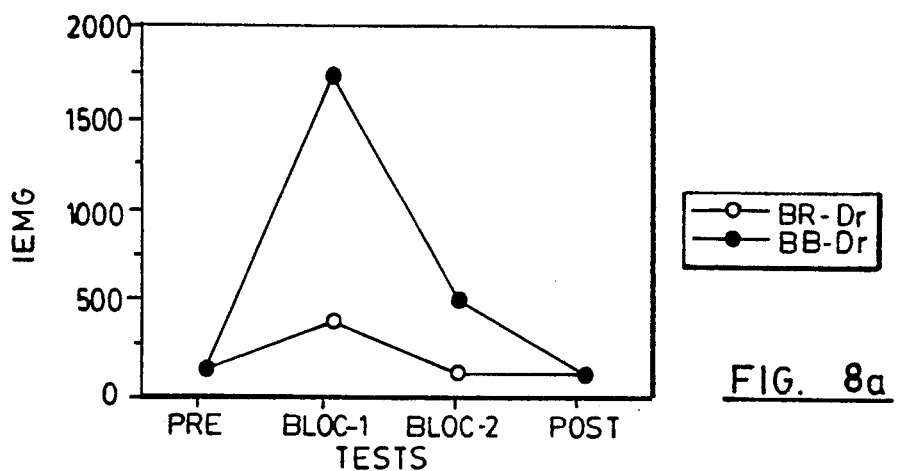
Figure 8B:
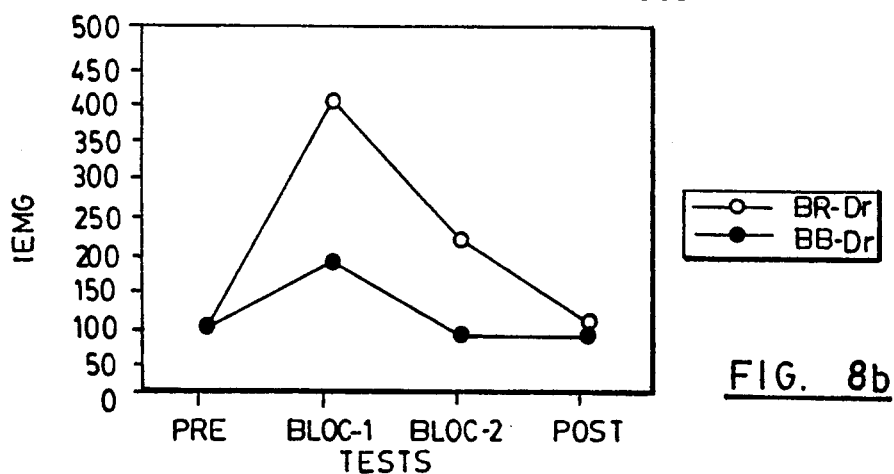

FIGS. 8a and b clearly illustrate the differences assessed between the two types of blocks. It is very interesting to note that the trend exhibited by the blocks on the first test (i.e., maintained effect up to the BLOCK-2 condition with the wooden blocks only) is reversed exactly on the second test (i.e., maintained effect up to the BLOCK-2 condition with the rubber blocks only). These results reveal that a longer term effect is added when the blocks are tested after another set of blocks.

The resting EMG results clearly show that rubber blocks according to the invention produce an increase in muscle tone on the right side, in a right-handed subject, when the blocks are placed respecting the procedures recommended in accordance with the invention for right-handers.

This increase in muscle tone, or resting EMG, can be controlled through different types of receptors: articular, cutaneous, or muscular However, the blocks significantly modifies the hip joint position, and it is well documented that passive joint movement changes the output of joint or articular receptors. Therefore, the more appealing theory to explain this increase in muscle tone is based upon the facilitatory action of the joint receptors upon muscular activity.

The test results reported hereinabove clearly show that the blocks according to the invention influence significantly the resting EMG or muscle tone. This increase in muscle tone seems to be controlled through the modulation of the gamma drive which is in turn controlled by the output of the joint receptors.

It is also very interesting to note the specificity of the effects of the blocks according to the invention. In the tested case, only the right side was affected by the blocks when the blocks were positioned to affect only that given side. It is then tempting to think that using the blocks according to the invention adequately can help to correct a muscular imbalance in the lower limbs.

I claim:

1. Method of chiropractic treatment with a person lying on his back, which comprises
   a) providing two blocks each of said blocks comprising:
      an elongated base having a front edge and a rear edge;
      a rear end face projecting upwardly from the rear edge of said base, said rear end face having an upper edge parallel to said base;
      an upper quadrilateral face parallel to said base and merging with the upper edge of said rear end face, said upper face having an inner edge opposite and parallel to said upper edge of said rear end face;
      a front end face projecting upwardly from a front edge of said base;
      an oblique portion extending between said upper face and said front end face, said oblique portion being generally inclined at about 60° to about 85° with respect to the vertical, and comprising:
         a first upper inwardly curved section descending from the inner edge of said upper face;
         a substantially intermediate flat quadrilateral face portion following said first upper cured portion;
         said quadrilateral flat face portion raising above said oblique portion and having a lower end so lifted as to form an angle of between about 7° and 9° with respect to a plane parallel to said oblique portion;
         a second lower inwardly curved section between said intermediate flat face and said front end face; and
      irregular lateral faces connecting said base, said first and said second curved sections, said flat portion, said upper face and merging into said front and rear end faces,
      wherein said block is made of soft rubbery material and said first and said second curved sections are formed with anti-skidding means capable of engaging a portion of a human body while preventing said portion from sliding along said curved sections;
   b) inserting one block underneath the person so as to reset below one ischium on one side of the person with said oblique portion of said one block placed against the body of the person, said one block being oriented transversely of the body of the person with the lower front corner pointing towards the groin area, and
   c) inserting a second block underneath the person with the oblique portion of said block immediately below the ischium on the other side of the person, with the upper front end corner pointing towards the groin area.

* * * * *